United States Patent
Yap et al.

(10) Patent No.: US 7,462,163 B2
(45) Date of Patent: Dec. 9, 2008

(54) SYSTEM AND METHOD FOR BLOCKAGE DETECTION FOR MEDICATION INFUSION

(75) Inventors: Marc Yap, Millville, UT (US); Sean B. Cahill, Temecula, CA (US); Jeffery T. Mason, Escondido, CA (US); Elizabeth A. Paderi, La Jolla, CA (US); Byron Hourmand, Vista, CA (US)

(73) Assignee: LMA North America, Inc., San Diego, CA (US)

( * ) Notice: Subject to any disclaimer, the term of this patent is extended or adjusted under 35 U.S.C. 154(b) by 100 days.

(21) Appl. No.: 10/903,951

(22) Filed: Jul. 30, 2004

(65) Prior Publication Data
US 2007/0078381 A1   Apr. 5, 2007

Related U.S. Application Data

(63) Continuation-in-part of application No. 10/218,106, filed on Aug. 12, 2002, now Pat. No. 6,893,414.

(51) Int. Cl.
*A61M 5/30* (2006.01)
*A61M 37/00* (2006.01)

(52) U.S. Cl. ......................................... 604/67; 604/131

(58) Field of Classification Search ............. 604/65–67, 604/131–157, 187, 891.1, 892.1, 6.11; 73/700, 73/706, 715, 730, 753; 417/44.9
See application file for complete search history.

(56) References Cited

U.S. PATENT DOCUMENTS

| | | | |
|---|---|---|---|
| 4,244,365 A | | 1/1981 | McGill et al. |
| 4,277,226 A | | 7/1981 | Archibald |
| 4,333,454 A | * | 6/1982 | Hargest, III ................... 604/28 |
| 4,369,780 A | * | 1/1983 | Sakai ........................... 604/123 |
| 4,526,574 A | * | 7/1985 | Pekkarinen ................. 604/505 |
| 4,563,179 A | * | 1/1986 | Sakai ........................... 604/245 |
| 4,702,675 A | * | 10/1987 | Aldrovandi et al. ........... 417/63 |
| 4,762,518 A | * | 8/1988 | Kreinick ..................... 604/245 |
| 4,882,575 A | | 11/1989 | Kawahara |
| 5,024,099 A | * | 6/1991 | Lee .............................. 73/730 |
| 5,098,380 A | * | 3/1992 | Aizawa et al. ................ 604/67 |
| 5,103,211 A | | 4/1992 | Daoud et al. |
| 5,116,203 A | | 5/1992 | Natwick et al. |
| 5,195,960 A | * | 3/1993 | Hossain et al. ................ 604/34 |
| 5,260,665 A | | 11/1993 | Goldberg et al. |

(Continued)

*Primary Examiner*—Kevin C Sirmons
*Assistant Examiner*—Elizabeth R MacNeill
(74) *Attorney, Agent, or Firm*—David W. Meibos; Barbara Daniels; Dan Justin

(57) ABSTRACT

A medication infusion system may include a controller and a reservoir module including a reservoir containing medication to be delivered to an internal wound site via the controller. The controller may have a peristaltic pump driven by a motor to urge medication to flow toward the internal wound site, through a conduit. A blockage sensor disables the motor and provides an alarm if the tube is blocked. The blockage sensor detects distention of a preferentially distendable portion of the tube, which may be routed about a constraining member. When blockage occurs, the tube distends preferentially along a direction generally parallel to the radius about which the tube bends. The blockage sensor may include a variety of switching elements, such as a pushbutton switch, a metal ring encircling the tube to make contact between conductors, and/ or a metal bridge bendable to make contact between conductors.

37 Claims, 8 Drawing Sheets

U.S. PATENT DOCUMENTS

| | | | |
|---|---|---|---|
| 5,342,298 A * | 8/1994 | Michaels et al. | 604/65 |
| 5,464,392 A | 11/1995 | Epstein et al. | |
| 5,483,222 A | 1/1996 | Tice | |
| 5,501,665 A | 3/1996 | Jhuboo et al. | |
| 5,647,853 A | 7/1997 | Feldmann et al. | |
| 5,657,000 A | 8/1997 | Ellingboe | |
| 5,695,473 A | 12/1997 | Olsen | |
| 5,720,721 A * | 2/1998 | Dumas et al. | 604/67 |
| 5,807,075 A * | 9/1998 | Jacobsen et al. | 417/44.2 |
| 5,807,322 A | 9/1998 | Lindsey et al. | |
| 5,827,223 A | 10/1998 | Butterfield | |
| 5,906,589 A | 5/1999 | Gordon et al. | |
| 5,935,106 A | 8/1999 | Olsen | |
| 5,954,696 A * | 9/1999 | Ryan | 604/141 |
| 5,989,222 A | 11/1999 | Cole et al. | |
| 6,358,225 B1 | 3/2002 | Butterfield | |
| 6,423,029 B1 | 7/2002 | Elsberry | |
| 6,523,414 B1 * | 2/2003 | Malmstrom et al. | 73/705 |
| 6,679,862 B2 * | 1/2004 | Diaz et al. | 604/151 |
| 6,830,558 B2 * | 12/2004 | Flaherty et al. | 604/67 |

\* cited by examiner

# SYSTEM AND METHOD FOR BLOCKAGE DETECTION FOR MEDICATION INFUSION

CROSS-REFERENCE TO RELATED APPLICATIONS

This application is a continuation-in-part of U.S. application Ser. No. 10/218,106, filed Aug. 12, 2002 now U.S. Pat. No. 6,893,414 and entitled INTEGRATED INFUSION AND ASPIRATION SYSTEM AND METHOD, the disclosure of which is incorporated herein by reference.

BACKGROUND OF THE INVENTION

1. The Field of the Invention

The present invention relates generally to the post-surgical treatment of closed wounds and specifically to methods and systems for infusion of a wound site to manage pain, swelling, bleeding and infection.

2. The Relevant Technology

One of the most difficult aspects of enduring a major surgical procedure is coping with the post-operative pain and swelling. Commonly, opioid analgesics, sometimes referred to as narcotics, are administered post-operatively to counter the pain associated with wound healing and recovery. However, the use of systemic opioid analgesics, whether administered by oral, intramuscular, or intravenous methods, includes a host of possible undesirable side effects, including: respiratory depression, renal function depression, nausea, constipation, ataxia, confusion, sweating, and itching. The length of hospital stay for patients undergoing a major surgical procedure is, in part, determined by the need to monitor and control the side effects of systemically administered opioid analgesics.

More recently, infusion pumps have been used to percutaneously deliver local anesthetics directly to the surgical wound. Thus, many of the undesirable side effects of systemic opioid analgesics are avoided. Furthermore, medication dosage is considerably less than systemic delivery since the medication is delivered directly to the affected site. However, contemporary percutaneous pain medication infusion pumps do not provide consistent relief of pain. Furthermore, many currently available medication infusion pumping arrangements are unable to adequately aspirate the affected site to reduce fluid build-up and swelling.

Yet further, many medication infusion pumps lack adequate safety measures to ensure that the proper dosage of medication is delivered. Some medication infusion pumps have safety measures that are too complex, and therefore cannot be reliably implemented, or that add unduly to the cost of the medication pump. Accordingly, existing medication infusion pumps may not be as cost-effective, failsafe, or easy to use as may be desirable.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
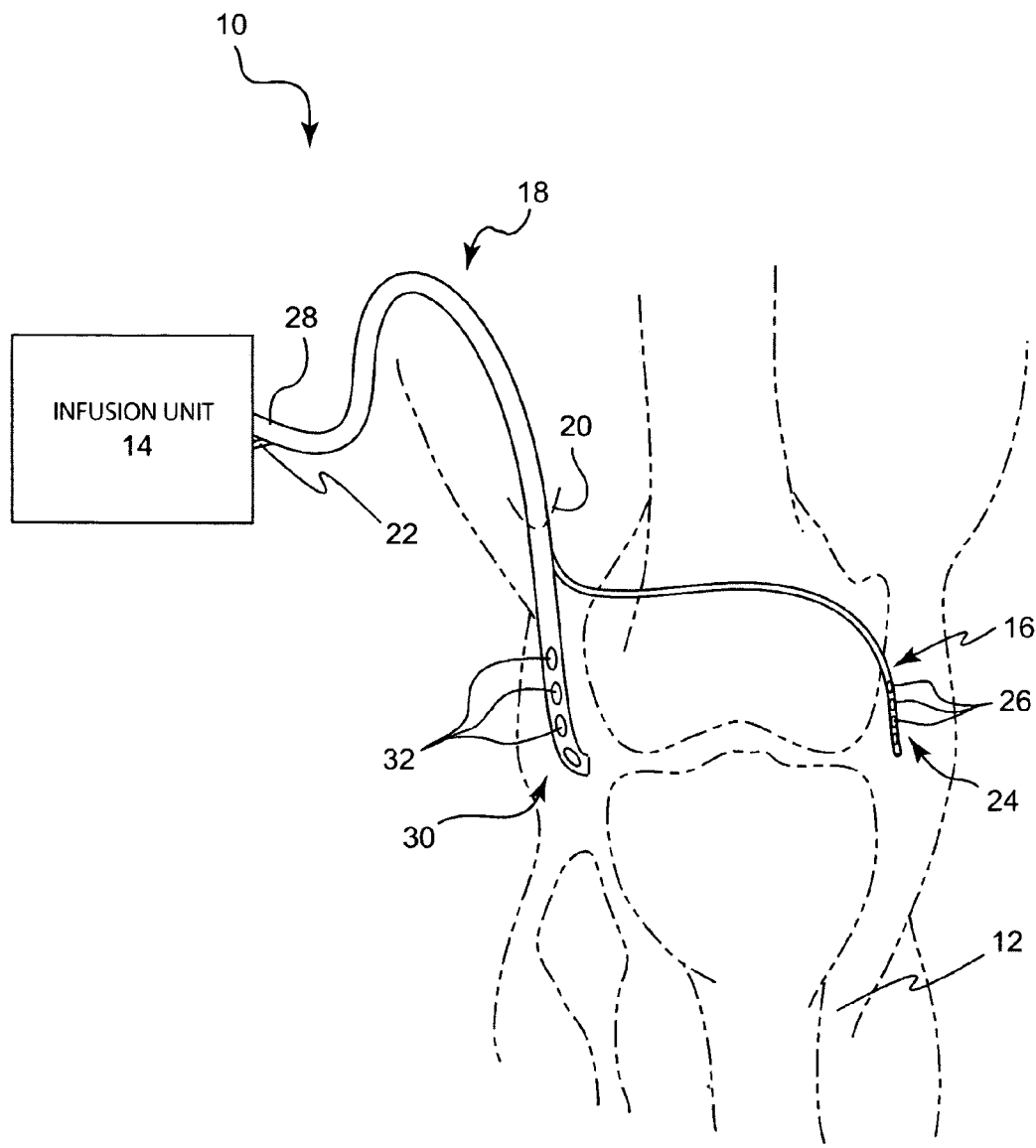
FIG. 1 is a schematic view of an integrated infusion and aspiration system applied to the knee of a patient.

Referring to FIG. 1, a schematic view illustrates an integrated infusion and aspiration system 10, or system 10, according to one embodiment of the invention. The system 10 may be postoperatively used to provide pain relief medication directly to an internal wound site 12. In FIG. 1, the internal wound site 12 is a knee that has been surgically treated, for example, via a partial or total knee arthroplasty. However, the systems and methods of the present invention are not limited to postoperative use, and may be used to relieve pain before or after treatment of injury to any part of the body. In addition to providing pain relief medication to the internal wound site 12, the system 10 aspirates internal fluids, such as spent medication and biological fluids, from the internal wound site 12.

In the embodiment of FIG. 1, the system 10 includes an integrated infusion and aspiration unit 14, hereinafter referred to as an infusion unit 14, that provides pressurized medication and provides a corresponding relative vacuum to receive fluids aspirated from the internal wound site 12. Additionally, the system 10 includes an infusion catheter 16 through which medication is delivered to the internal wound site 12, and an aspiration catheter 18 through which fluids are received in the infusion unit 14 from the internal wound site 12. As shown, a portion of the infusion catheter 16 may be nested within a corresponding portion of the aspiration catheter 18 so that both catheters 16, 18 gain access to the internal wound site 12 through a single point-of-entry 20.

As illustrated, the infusion catheter 16 has a proximal end 22 and a distal end 24, with a plurality of flow orifices 26 arrayed along the distal end 24 to provide infusion of medication along a relatively broad dispersal path within the internal wound site 12. Similarly, the aspiration catheter 18 has a proximal end 28 and a distal end 30, with a plurality of flow orifices 32 arranged along the distal end 30 to receive fluids from a relatively broad area of the internal wound site 12. The proximal end 22 of the infusion catheter 16 is generally nested within the proximal end 28 of the aspiration catheter 18 so that medication moves toward the internal wound site 12 through the infusion catheter 16, and fluids are removed from the internal wound site 12 through the distal end 30 of the aspiration catheter 18, and then through the generally annular space between the proximal ends 22, 28 of the catheters 16, 18.

Figure 2:
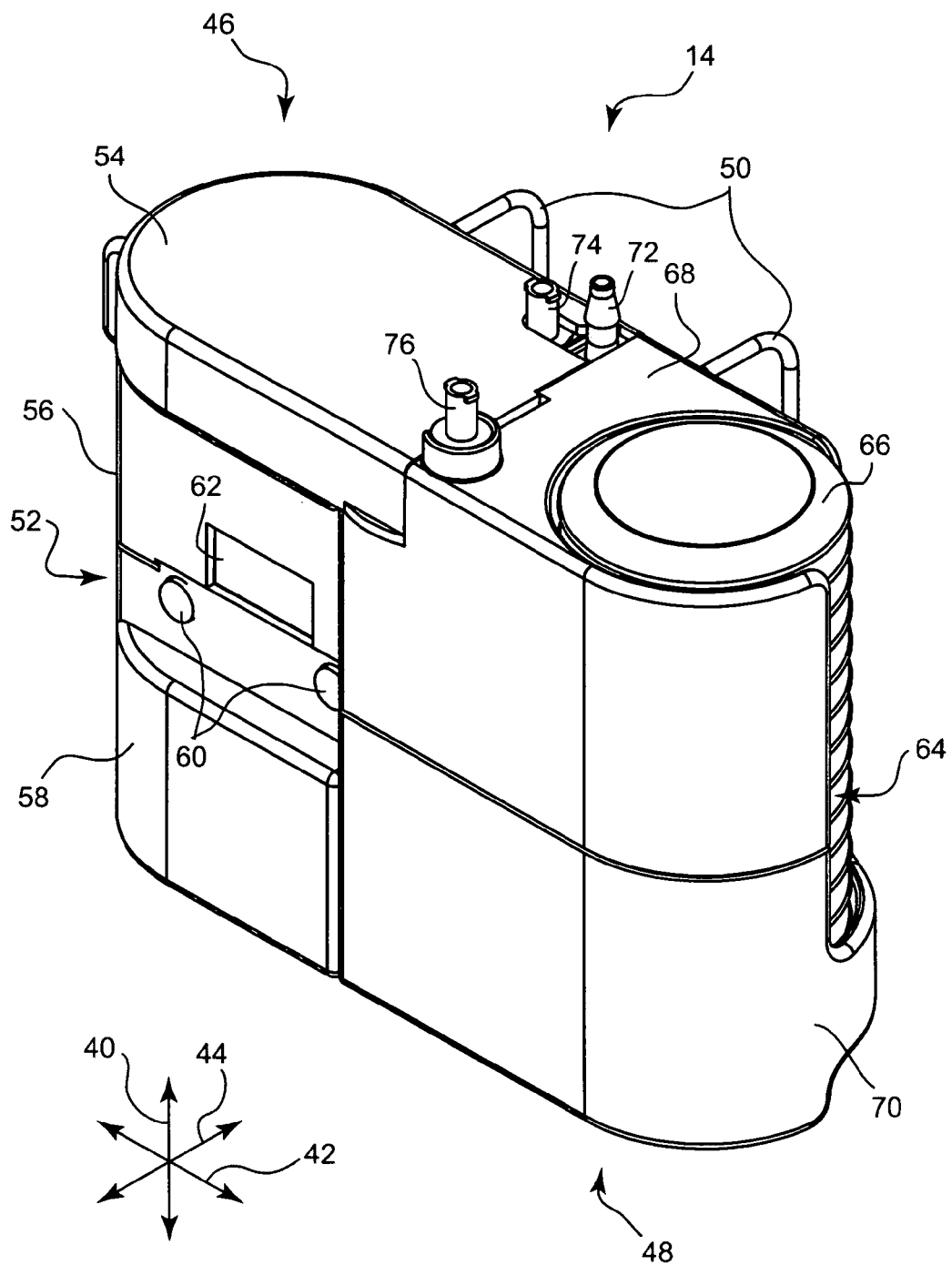
FIG. 2 is a perspective view of the integrated infusion and aspiration system of FIG. 1, in a fully-assembled state.

Referring to FIG. 2, a perspective view illustrates the infusion unit 14 of the system 10 of FIG. 1, without the catheters 16, 18. The infusion unit 14 has a longitudinal direction 40, a lateral direction 42, and a transverse direction 44, which are oriented as illustrated by the arrows in FIG. 2. The infusion unit 14 has a controller 46 and a reservoir module 48. The reservoir module 48 contains medication to be provided to the internal wound site 12 and fluids aspirated from the internal wound site 12. The controller 46 provides the necessary pressure differentials to control infusion of medication to the internal wound site 12 and aspiration of fluids from the internal wound site 12. The infusion unit 14 may also have a pair of mounting brackets 50 or other attachment devices that can be used to attach the infusion unit 14 to a mobile rack, hospital bed frame, or other piece of hospital equipment.

The controller 46 has a main body 52 that contains most of the internal components (not shown) of the controller 46, and a cap 54 that can be removed to couple the controller 46 to the reservoir module 48 in a manner that will be shown and described in greater detail subsequently. The main body 52 has a first portion 56 and a second portion 58 that are attached together via relative motion in the longitudinal direction 40 to encase the internal components, as will also be shown and described in greater detail. The controller 46 has controls such as buttons 60 that can be used by medical personnel to control the operation of the controller 46. Additionally, the controller 46 may have a display 62 that may show information such as infusion and aspiration history, the current operational mode of the controller 46, and the like.

The reservoir module 48 has a reservoir retainer 64 that serves to retain a first reservoir (not shown in FIG. 2) and a second reservoir 66. The first reservoir contains medication to be infused into the internal wound site 12 and the second reservoir 66 receives fluid aspirated from the internal wound site 12. The reservoir retainer 64 has a first portion 68 and a second portion 70 that are attached together along the longitudinal direction 40 in a manner similar to that of the first and second portions 56, 58 of the main body 52 of the controller 46. Additionally, the reservoir module 48 has an infusion port 72 shaped to be connected to the proximal end 22 of the infusion catheter 16 and an aspiration port 74 shaped to be connected to the proximal end 28 of the aspiration catheter 18. A fill port 76 is shaped to be connected to a supply of medication to enable the first reservoir to be filled without removing it from the reservoir retainer 64.

The controller 46 and the reservoir module 48 are coupled together in a manner that is simple and relatively failsafe, for example, through the use of mating surfaces (not shown) of the controller 46 and the reservoir module 48 that interlock via dovetail features or the like. The controller 46 may be coupled to any of multiple reservoir modules, not all of which need have the same configuration as the reservoir module 48. For example, in alternative embodiments of the invention, a reservoir module may have only a single reservoir for infusion. The controller 46 may be connectable to such a reservoir module in a manner similar to that of the reservoir module 48.

During setup or use, it is conceivable that the infusion catheter 16 may become blocked, for example, by incorrect placement of the distal end 24, by the presence of an object within the infusion catheter 16, or by compression of some part of the infusion catheter 16 by other external objects. It would be desirable to have some method by which blockage of the infusion catheter 16 could be detected to ensure that, if the medication not properly delivered to the internal wound site 12, medical personnel can be notified and the infusion unit 14 can take appropriate corrective action, such as ceasing to provide infusion and aspiration until the blockage is removed. One embodiment of such a blockage sensor will be shown and described in connection with FIGS. 3 and 4, as follows.

Figure 3:
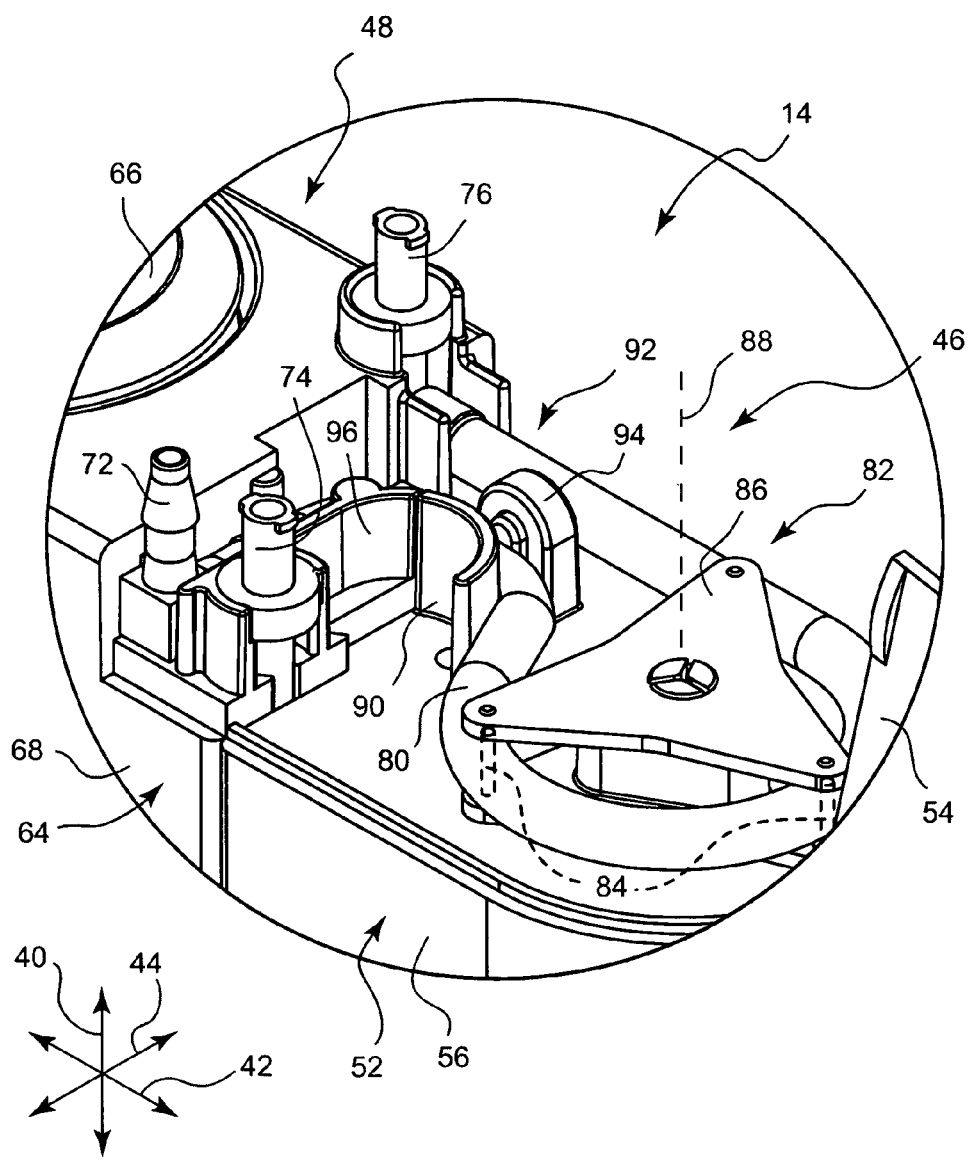
FIG. 3 is an enlarged, perspective view of a portion of the controller of the integrated infusion and aspiration system of FIG. 1.

Referring to FIG. 3, an enlarged, perspective view illustrates the upper end of the infusion unit 14 with the cap 54 withdrawn to reveal internal components. As shown, the reservoir module 48 has a conduit, which may take the form of a tube 80, that extends in a generally circular pathway from a location in communication with the fill port 76 to convey medication to the infusion port 72. In this application, the term "conduit" refers to a fluid conveying structure with any cross sectional shape. Accordingly, a "conduit" need not necessarily be a tube. In alternative embodiments, a controller, rather than a reservoir module, may have a tube that serves the same function as the tube 80.

The controller 46 has a pump 82, which may take the form of a peristaltic pump designed to compress a portion of the tube 80 and to move the compressed portion along the tube 80 to urge the medication to move through the tube 80 in a highly controllable manner. The pump 82 may include a plurality of rotors 84 retained by a rotor carriage 86 that rotates about an axis of rotation 88 to move the rotors 84 along a circular path. The rotor carriage 86 is driven by a motor (not shown in FIG. 3) that provides rotational output about the axis of rotation 88.

The rotors 84 may take the form of small-diameter cylindrical rollers that are able to roll along the exterior of the tube 80. The tube 80 may be "tightly routed," or stretched tightly around the rotors 84 such that the tube 80 is pinched relatively tightly proximate each of the rotors 84, so that medication is generally unable to flow into the infusion catheter 16 in the absence of motion of the rotors 84. The cap 54 is generally shaped to cover the tube 80, the rotors 84, and the rotor carriage 86 to prevent external objects from interfering with the operation of the pump 82.

The present invention envisions the use of a wide variety of different types of pumps. For example, peristaltic pumps need not involve stretching of a conduit about the rotors, but may instead be based upon compression of the conduit by the rotors against an opposing surface, such as a generally cylindrical interior wall. Indeed, a controller according to the present invention need not have a peristaltic pump, but may instead use a different type of pump such as a screw pump, a rotary vane pump, a rod-and-piston pump, or any other known type of pump.

The controller 46 also has a constraining member in the form of an arcuate wall 90 that abuts a portion of the tube 80 to control the path of the tube 80 around the rotors 84. The arcuate wall 90 also causes the tube 80 to assume a generally oval cross section proximate the arcuate wall to enhance the operation of a blockage sensor 92 by providing a preferentially distendable portion of the tube 80. A "preferentially distendable portion" is a portion of a pressure-bearing structure that expands in an amplified manner in response to increases in internal pressure, when compared to adjacent portions of the pressure-bearing structure.

The blockage sensor 92 is designed to sense preferential distention of the portion of the tube 80 proximate the arcuate wall 90 to determine whether the tube 80 or the infusion catheter 16 has been pinched or blocked. Accordingly, the blockage sensor 92 includes a switch that either closes or opens a circuit in response to abnormal distention of the tube 80. Closing or opening the circuit may trigger cessation of infusion and/or aspiration, production of an audible alarm tone, or the like.

In FIG. 3, the switch of the blockage sensor 92 takes the form of a button 94 that can be compressed to cause conductors within the button 94 to contact each other, thereby closing the circuit. The button 94 may extend upward from a circuit board (not shown) that controls the operation of the controller 46 and lies generally coplanar with the display 62 illustrated in FIG. 2. Indeed, the circuit board may have a continuous expanse of substrate that extends from behind the display 62 into the button 94.

In the embodiment of FIG. 3, the blockage sensor 92 is mechanically operated, or switched based on exertion of mechanical force against the button 94. The button 94 is only one of many mechanically operated switch types that may be used to provide a blockage sensor. Furthermore, in the alternative to mechanical operation, a blockage sensor of the present invention may have a switch that is operated based on a different type of input, such as an optical or magnetic input. An optical switch may detect distention by sensing the silhouette of the tube 80, by sensing optically recognizable markings on the tube 80, or by sensing repositioning of a shutter or plate to occlude or reveal a light source near the tube 80. A magnetic switch may detect distention by sensing repositioning of a magnet or a low-reluctance material coupled to the tube 80, or the like. Other sensor types in addition to magnetic or optical sensors may be used.

In FIG. 3, the blockage sensor 92 is part of the controller 46. In alternative embodiments, a blockage sensor could be part of a reservoir module such as the reservoir module 48. A blockage sensor may even be a separate component that can be selected and installed independently of the controller and reservoir module.

Referring again to the embodiment of FIG. 3, the reservoir module 48 may have a second constraining member, which takes the form of an arcuate wall 96 adjoining the arcuate wall 90 of the controller 46. The arcuate walls 90, 96 may provide a relatively continuous surface about which the tube 80 bends at a relatively constant radius. The arcuate walls 90, 96 operate to broaden the adjoining portion of the tube 80 along the longitudinal direction 40, while constraining the adjoining portion along the lateral and transverse directions 42, 44. The function of such constraint and the operation of the blockage sensor 92 will be shown and described in greater detail in connection with FIG. 4.

In alternative embodiments, a wide variety of constraining members may be used. For example, the tube 80 may be routed about one or more constraining members that define a non-arcuate shape. The tube 80 may alternatively have a preferentially distendable portion that is not routed about a constraining member, but is instead compressed, for example, via placement between two constraining members, such as walls, pins, or the like, that are relatively closely spaced together. A constraining member may be positioned on the controller 46 or on the reservoir module 48. Alternatively, as in the embodiment of FIG. 3, constraining members may be present on both the controller 46 and the reservoir module 48.

In yet other alternative embodiments, no constraining member need be provided. For example, the tube 80 may have a preferentially distendable portion that is formed of a more elastic material than the remainder of the tube. Alternatively, the preferentially distendable portion may have a smaller wall thickness than the remainder of the tube. As yet another alternative, the preferentially distendable portion may have an opening in the tube wall in which a flexible patch is positioned to provide enhanced distention. In all of the above embodiments, distention of the preferentially distendable portion is amplified beyond that of the surrounding portions of the tube 80 without constraining the diameter of the tube 80 or bending the tube 80. Other methods of providing the preferentially distendable portion may also be used within the scope of the present invention.

Figure 4:
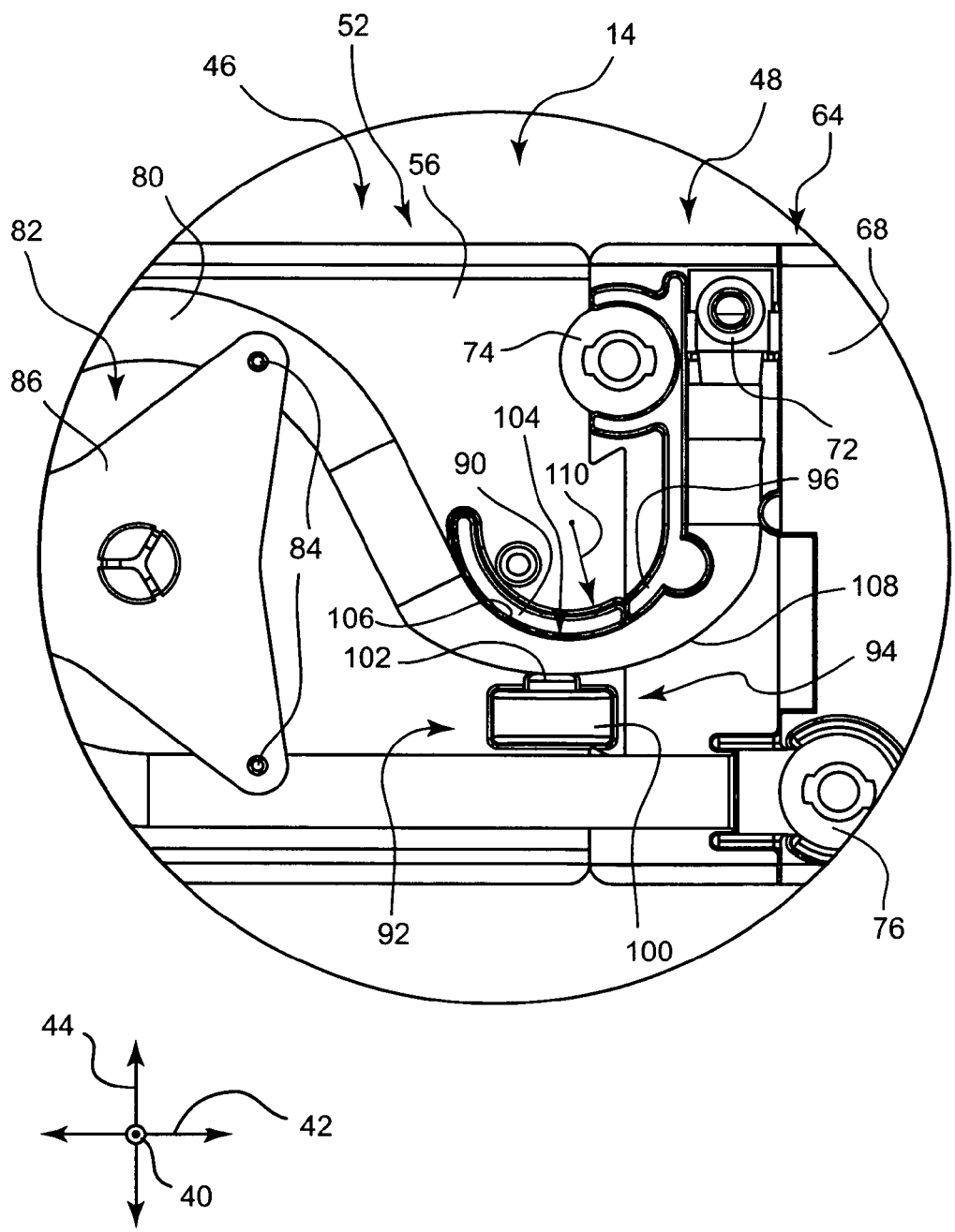
FIG. 4 is an enlarged, plan view of a portion of the controller of the integrated infusion and aspiration system of FIG. 1.

Referring to FIG. 4, an enlarged, plan view illustrates a central portion of the infusion unit 14. As shown, the button 94 has a main body portion 100 and a plunger portion 102. The plunger portion 102 may be movable into the main body portion 100 to cause the contacts to touch each other. If desired, the entire button 94 may be covered by an electrically insulative layer such as a rubber cover or the like.

The portion of the tube 80 that is routed about the arcuate walls 90, 96 may be termed a preferentially distendable portion 104 because the arcuate walls 90, 96 contact the exterior of the tube 80 in such a manner as to compress its cross section along at least one direction. The preferentially distendable portion 104 has an inside wall 106 on the inside arc of the preferentially distendable portion 104 and an outside wall 108 on the outside arc of the preferentially distendable portion 104. The preferentially distendable portion 104, or more specifically, the inside wall 106, has a radius 110 about which the preferentially distendable portion 104 curves to lie along the adjacent surfaces of the arcuate walls 90, 96. Accordingly, the radius 110 may also be the radius of curvature of the adjacent surfaces of the arcuate walls 90, 96.

The effect of routing the preferentially distendable portion 104 about the arcuate walls 90, 96 is to cause the diameter of the preferentially distendable portion 104 to be constrained, i.e., limited or compressed, along a direction parallel to the radius 110. The radius 110 is not only at the position shown, but extends to a generally continuous, semicircular arc defined by the arcuate walls 90, 96. Accordingly, the diameter of the preferentially distendable portion 104 is constrained along the lateral direction 42, the transverse direction 44, or a direction having lateral and transverse components, depending on where the diameter is measured along the preferentially distendable portion 104. The diameter of the preferentially distendable portion 104 may generally be extended along a direction perpendicular to the radius 110, i.e., along the longitudinal direction 40.

As a result of the extension of the preferentially distendable portion 104 along the longitudinal direction 40, fluid pressure presses outward against the wall of the preferentially distendable portion 104 along a comparatively larger area parallel to the radius 110. As a result, in response to internal fluid pressure, the preferentially distendable portion 104 distends preferentially along a direction generally parallel to the radius 110. Accordingly, a pressure increase resulting from blockage or pinching of the tube 80 or the infusion catheter 16 will cause an amplified increase in the diameter of the preferentially distendable portion 104, in a direction parallel to the radius 110. Such an amplified distention is more easily measured than a smaller distention.

In this application, "measure" may mean obtaining a numerical measurement, or simply a binary indication of whether a dimension is greater or less than a critical value. "Preferential distention" refers to distention that is larger along one direction than along another. Hence, the preferentially distendable portion 104 may undergo less distention perpendicular to the radius 110, i.e., along the longitudinal direction 40, than parallel to the radius 110.

The blockage sensor 92 uses the preferential distention of the preferentially distendable portion 104 along the radius 110 to facilitate detection of blockage of the tube 80 or infusion catheter 16. More precisely, the button 94 is displaced from the preferentially distendable portion 104 along the transverse direction 44, and is positioned adjacent to the preferentially distendable portion 104 such that distention of the preferentially distendable portion along the transverse direction 44 will move the plunger portion 102 with respect to the main body portion 100, thereby closing a circuit (not shown) to trigger an alarm, cessation of operation of the infusion unit 14, and/or the like. The preferential distention of the preferentially distendable portion 104 helps to more reliably close the circuit when blockage occurs, while avoiding closure of the circuit when there is no blockage (such as when some smaller amount of distention occurs due to startup of the pump 82 or a similar transient condition).

The blockage sensor 92 is only one potential type of blockage sensor that may be used in connection with the present invention. In alternative embodiments, a wide variety of different sensor types may be used in place of the blockage sensor 92. Such sensors may open a circuit rather than closing it, and may use switches configured differently from the button 94. FIGS. 5-8 provide a variety of alternative embodiments, which will be described in detail as follows.

Figure 5:
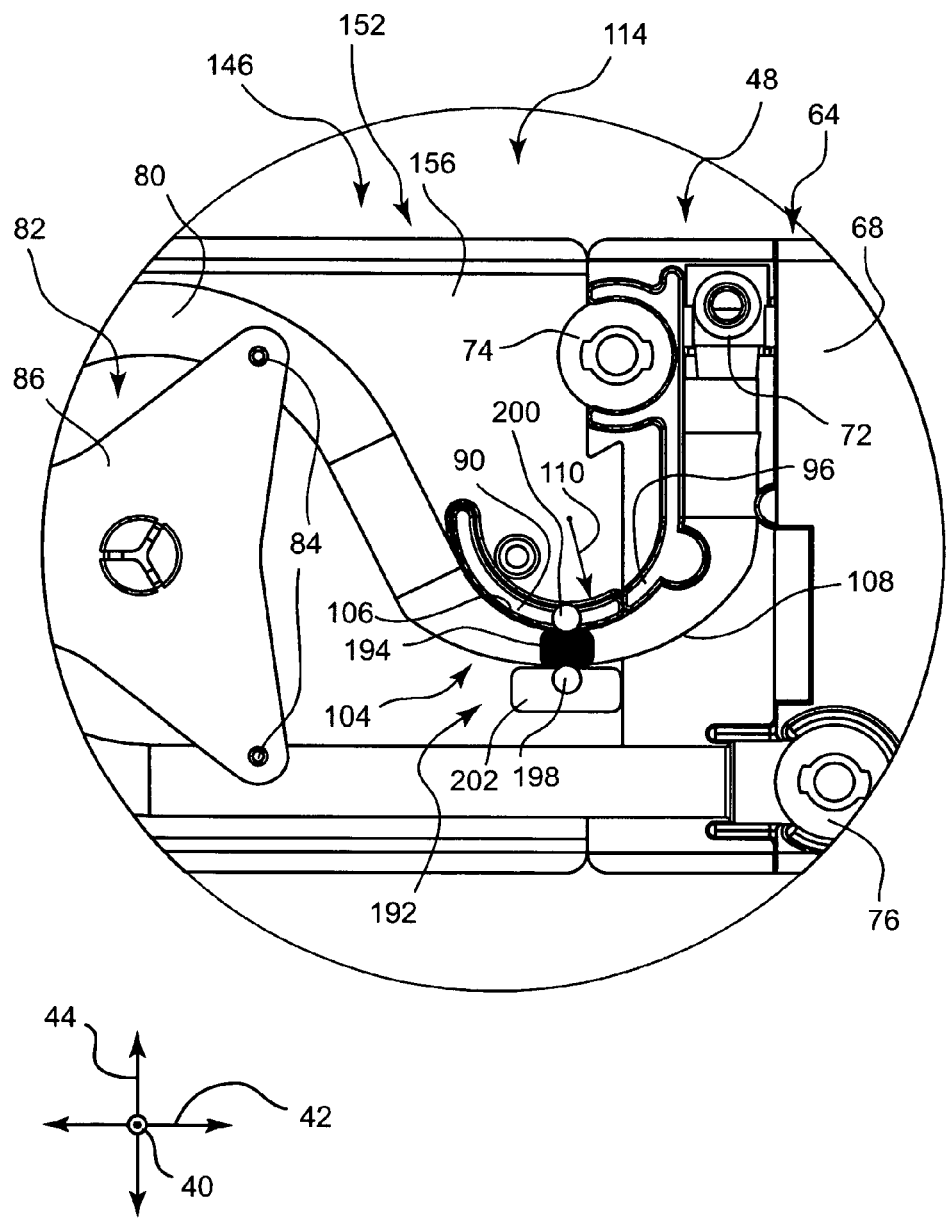
FIG. 5 is an enlarged, plan view of a portion of a controller of an infusion system according to one alternative embodiment of the invention.

Referring to FIG. 5, an enlarged, plan view illustrates an infusion unit 114 according to one alternative embodiment of the invention. The infusion unit 114 may be used as part of an infusion system such as the infusion system 10 of FIG. 1. Like the infusion unit 14 of the previous embodiment, the infusion unit 14 has a controller 146 and a reservoir module 48. The reservoir module 48 may be identical to that of FIG. 2, while the controller 146 has a configuration somewhat different from the controller 46 of FIG. 2.

The controller 146 may have a main body 152 and a cap (not shown). Like the main body 52 of the previous embodiment, the main body 152 has a first portion 156 and a second portion (not shown). Furthermore, the controller 146 has a pump 82 designed to urge medication to move through a tube 80 of the reservoir module 48. As in the previous embodiment, the tube 80 is routed about an arcuate wall 90 and a second arcuate wall 96 to provide a preferentially distendable portion 104 having a generally arcuate shape with a radius 110. The controller 146 has a blockage sensor 192 that utilizes preferential distention of the preferentially distendable portion 104 along the radius 110 to facilitate detection of a blockage condition.

In the embodiment of FIG. 5, the blockage sensor 192 has a first conductor that takes the form of a stent 194 encircling the diameter of the preferentially distendable portion 104. The stent 194 is formed of an electrically conductive material such as a metal, and may comprise a solid band of material, a mesh, or some other structure. The stent 194 fits tightly around the exterior of the preferentially distendable portion 104 and has a geometry selected to permit the stent 194 to deform along with deformation of the exterior wall of the preferentially distendable portion 104. Accordingly, when the diameter of the preferentially distendable portion 104 distends along the radius 110, the stent 194 also distends, thereby assuming a shape that is broader along the transverse direction 44.

In addition to the stent 194, the blockage sensor 192 may include second and third conductors that take the form of pins 198, 200 that extend generally along the longitudinal direction 40 and are positioned transversely on either side of the stent 194. The pin 200 may be positioned in an alcove in the surface of the arcuate wall 90 such that the pin 200 is continuously in contact with the stent 194, but does not impinge upon the preferentially distendable portion 104 so as to avoid restricting fluid flow through the preferentially distendable portion 104. The pin 198 is positioned on the opposite side of the stent 194 from the pin 200, and is displaced from the stent 194 under normal operating conditions so as to avoid making electrical contact with the stent 194.

When distention occurs, the stent 194 expands along the transverse direction 44 to contact the pin 198. Electrical current is able to move from the pin 200 to the pin 198 via the stent 194. Accordingly, as in the previous embodiment, a circuit has been closed via preferential distention of the preferentially distendable portion 104. Closure of the circuit triggers an alarm, cessation of operation of the infusion unit 114, and/or the like.

Figure 6:
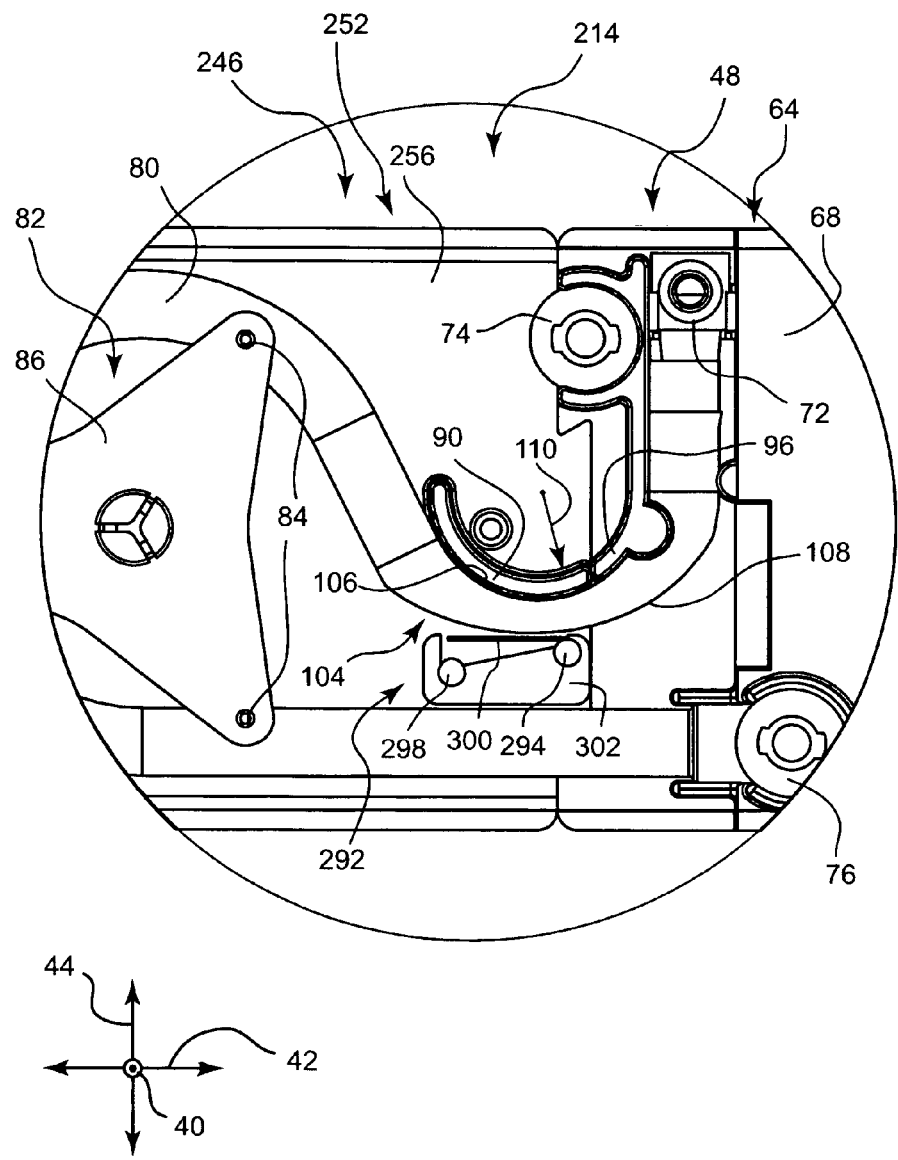
FIG. 6 is an enlarged, plan view of a portion of a controller of an infusion system according to another alternative embodiment of the invention.

Referring to FIG. 6, an enlarged, plan view illustrates an infusion unit 214 according to one alternative embodiment of the invention. The infusion unit 214 may be used as part of an infusion system such as the infusion system 10 of FIG. 1. Like the infusion unit 14 of the first embodiment, the infusion unit 214 has a controller 246 and a reservoir module 48. The reservoir module 48 may be identical to that of FIG. 2, while the controller 246 has a configuration somewhat different from that of the controller 46.

The controller 246 may have a main body 252 and a cap (not shown). Like the main body 52 of the first embodiment, the main body 252 has a first portion 256 and a second portion (not shown). Furthermore, the controller 246 has a pump 82 designed to urge medication to move through a tube 80 of the reservoir module 48. As in the first embodiment, the tube 80 is routed about an arcuate wall 90 and a second arcuate wall 96 to provide a preferentially distendable portion 104 having a generally arcuate shape with a radius 110. The controller 246 has a blockage sensor 292 that utilizes preferential distention of the preferentially distendable portion 104 along the radius 110 to facilitate detection of a blockage condition.

In the embodiment of FIG. 6, the blockage sensor 292 has a first conductor and a second conductor, which may take the form of a pin 294 and a pin 298, respectively. The pins 294, 298 are displaced from each other along the lateral direction 42 and extend along the longitudinal direction 40 to make electrical contact with a circuit board or the like (not shown). The pins 294, 298 are offset from the preferentially distendable portion 104 along the transverse direction 44.

The blockage sensor 292 also has a conductive bridge 300, which may be formed of a thin metal shim or the like. The conductive bridge 300 is rigidly affixed to the pin 294 and extends along the lateral direction 42 such that the free end of the conductive bridge 300 is between the preferentially distendable portion 104 and the pin 298. The pins 294, 298 may be retained by a casing 302 that does not conduct current between the pins 294, 298, but keeps the pins 294, 298 in place while permitting bending of the conductive bridge 300.

When the preferentially distendable portion 104 distends preferentially along the transverse direction 44, the preferentially distendable portion 104 contacts the conductive bridge 300 and bends the conductive bridge 300 along the transverse direction 44 so that the free end of the conductive bridge 300 makes electrical contact with the pin 298. Electrical current is able to move from the pin 294 to the pin 298 via the conductive bridge 300. Accordingly, as in the first embodiment, a circuit has been closed via preferential distention of the preferentially distendable portion 104. Closure of the circuit triggers an alarm, cessation of operation of the infusion unit 214, and/or the like.

Figure 7:
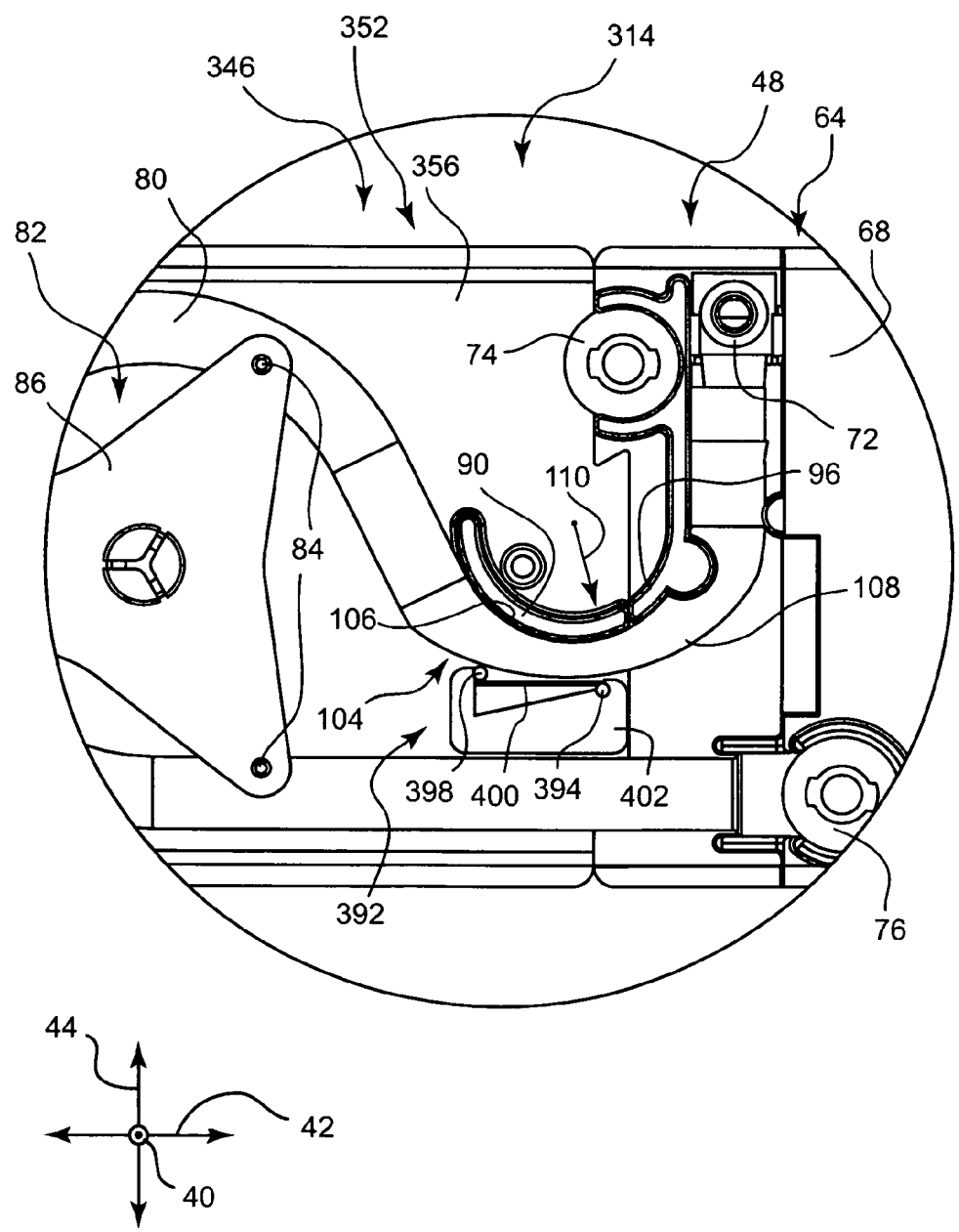
FIG. 7 is an enlarged, plan view of a portion of a controller of an infusion system according to yet another alternative embodiment of the invention.

Referring to FIG. 7, an enlarged, plan view illustrates an infusion unit 314 according to one alternative embodiment of the invention. The infusion unit 314 may be used as part of an infusion system such as the infusion system 10 of FIG. 1. Like the infusion unit 14 of the first embodiment, the infusion unit 314 has a controller 346 and a reservoir module 48. The reservoir module 48 may be identical to that of FIG. 2, while the controller 346 has a configuration somewhat different from that of the controller 46.

The controller 346 may have a main body 352 and a cap (not shown). Like the main body 52 of the first embodiment, the main body 352 has a first portion 356 and a second portion (not shown). Furthermore, the controller 346 has a pump 82 designed to urge medication to move through a tube 80 of the reservoir module 48. As in the first embodiment, the tube 80 is routed about an arcuate wall 90 and a second arcuate wall 96 to provide a preferentially distendable portion 104 having a generally arcuate shape with a radius 110. The controller 346 has a blockage sensor 392 that utilizes preferential distention of the preferentially distendable portion 104 along the radius 110 to facilitate detection of a blockage condition.

In the embodiment of FIG. 7, the blockage sensor 392 has a first conductor and a second conductor, which may take the form of a pin 394 and a pin 398, respectively. The pins 394, 398 are displaced from each other generally along the lateral direction 42 and extend along the longitudinal direction 40 to make electrical contact with a circuit board or the like (not shown). The pins 394, 398 are offset from the preferentially distendable portion 104 along the transverse direction 44.

The blockage sensor 392 also has a conductive bridge 400, which may be formed of a thin metal shim or the like. The conductive bridge 400 is rigidly affixed to the pin 394 and extends along the lateral direction 42 such that the pin 398 is between the free end of the conductive bridge 400 and the preferentially distendable portion 104. Under normal conditions, the free end of the conductive bridge 400 contacts the pin 398. The pins 394, 398 may be retained by a casing 402 that does not conduct current between the pins 394, 398, but keeps the pins 394, 398 in place while permitting bending of the conductive bridge 400.

When the preferentially distendable portion 104 distends preferentially along the transverse direction 44, the preferentially distendable portion 104 contacts the conductive bridge 400 and bends the conductive bridge 400 along the transverse direction 44 so that the free end of the conductive bridge 400 moves away from the pin 398 to break from electrical contact with the pin 398. Electrical current is no longer able to move from the pin 394 to the pin 398 via the conductive bridge 400. Accordingly, by contrast with the previous embodiments, a circuit has been opened, not closed, via preferential distention of the preferentially distendable portion 104. Opening of the circuit triggers an alarm, cessation of operation of the infusion unit 314, and/or the like.

Figure 8:
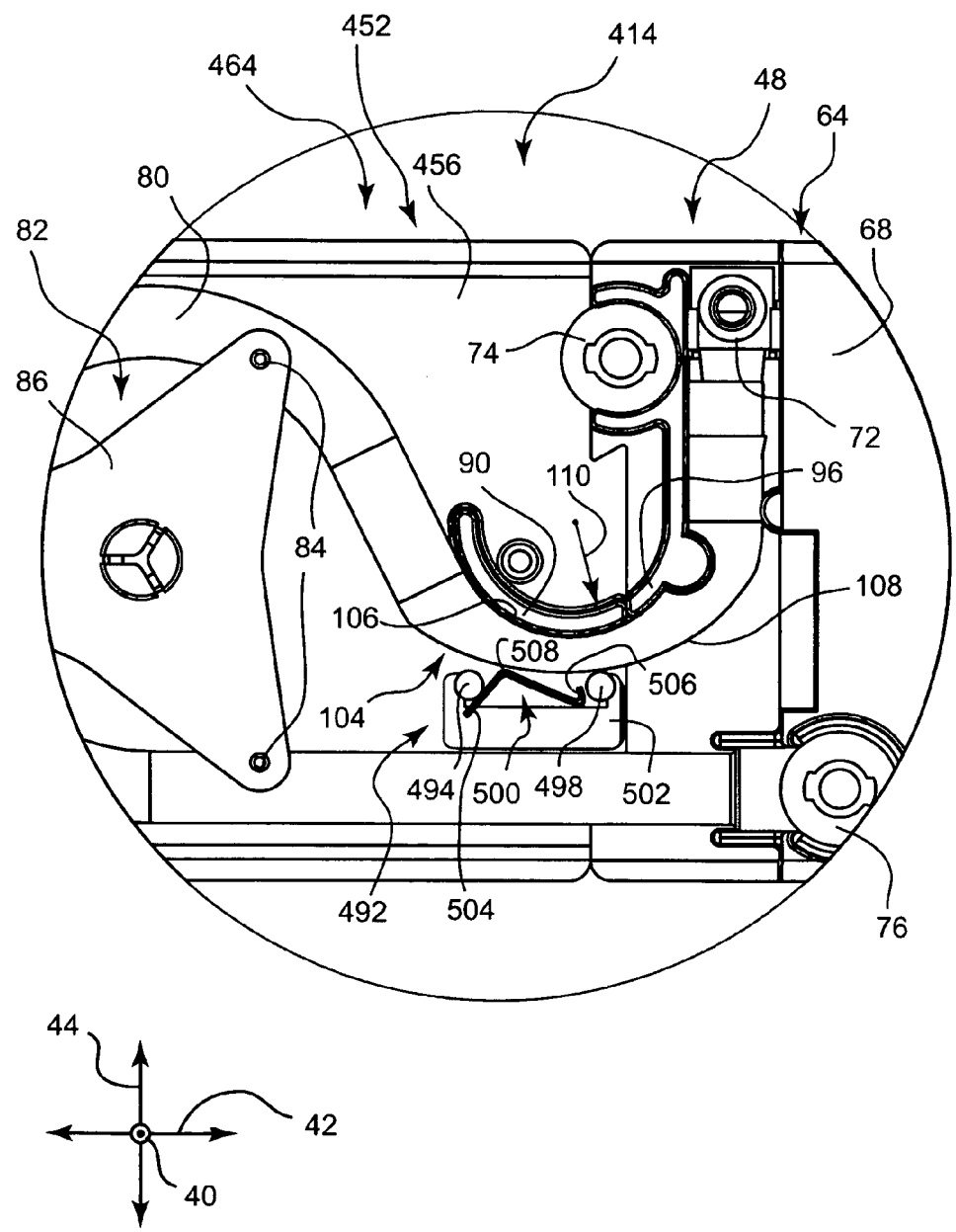
FIG. 8 is an enlarged, plan view of a portion of a controller of an infusion system according to still another alternative embodiment of the invention.

Referring to FIG. 8, an enlarged, plan view illustrates an infusion unit 414 according to one alternative embodiment of the invention. The infusion unit 414 may be used as part of an infusion system such as the infusion system 10 of FIG. 1. Like the infusion unit 14 of the first embodiment, the infusion unit 414 has a controller 446 and a reservoir module 48. The reservoir module 48 may be identical to that of FIG. 2, while the controller 446 has a configuration somewhat different from that of the controller 46.

The controller 446 may have a main body 452 and a cap (not shown). Like the main body 52 of the first embodiment, the main body 452 has a first portion 456 and a second portion (not shown). Furthermore, the controller 446 has a pump 82 designed to urge medication to move through a tube 80 of the reservoir module 48. As in the first embodiment, the tube 80 is routed about an arcuate wall 90 and a second arcuate wall 96 to provide a preferentially distendable portion 104 having a generally arcuate shape with a radius 110. The controller 446 has a blockage sensor 492 that utilizes preferential distention of the preferentially distendable portion 104 along the radius 110 to facilitate detection of a blockage condition.

In the embodiment of FIG. 8, the blockage sensor 492 has a first conductor and a second conductor, which may take the form of a pin 494 and a pin 498, respectively. The pins 494, 498 are displaced from each other along the lateral direction 42 and extend along the longitudinal direction 40 to make electrical contact with a circuit board or the like (not shown). The pins 494, 498 are offset from the preferentially distendable portion 104 along the transverse direction 44.

The blockage sensor 492 also has a conductive bridge 500, which may be formed of a thin metal shim or the like. The conductive bridge 500 may be rigidly affixed proximate the pin 494 and extends along the lateral direction 42 to a position proximate the pin 498. The pins 494, 498 may be retained by a casing 502 that does not conduct current between the pins 494, 498, but keeps the pins 494, 498 in place while permitting bending and sliding of the conductive bridge 500.

The conductive bridge 500 has a first end 504 that is seated in the casing 502 proximate the pin 494, and a second end 498 that is free of constraint and is positioned between the pins 494, 498, adjacent to the pin 498. The conductive bridge 500 also has a bend 508 positioned between the first and second ends 504, 506. The bend 508 lies adjacent to the preferentially distendable portion 104. The bend 508 may comprise a sharp bend, as shown in FIG. 8, or a more gentle curvature. The bend 508 of FIG. 8 also has an obtuse angle, but alternative embodiments may use a wide variety of different angles.

When the preferentially distendable portion 104 distends preferentially along the transverse direction 44, the preferentially distendable portion 104 contacts the bend 508 of the conductive bridge 500 and bends the portion of the conductive bridge 500 between the bend 508 and the first end 504 along the transverse direction 44. The portion of the conductive bridge 500 between the bend 508 and the second end 506 assumes an angle closer to the lateral direction 42.

The bending and reorientation of the conductive bridge 500 cooperate to cause the second end 508 to slide along the adjacent surface of the casing 502 and extend along the lateral direction 42 toward the pin 498. The motion of the conductive bridge 500 serves to amplify the motion of the second end 506 such that the second end 506 moves further than the bend 508. Accordingly, the operation of the blockage sensor 492 is enhanced not only via preferential distention of the diameter of the preferentially distendable portion 104, but also by the kinematics provided by the conductive bridge 500. The motion of the conductive bridge 500 thus further helps to more reliably close the circuit when blockage occurs, while avoiding closure of the circuit when there is no blockage.

The second end 508 moves far enough to make electrical contact with the pin 498. Electrical current is then able to move from the pin 494 to the pin 498 via the conductive bridge 500. Accordingly, as in the first embodiment, a circuit has been closed via preferential distention of the preferentially distendable portion 104. Closure of the circuit triggers an alarm, cessation of operation of the infusion unit 414, and/or the like.

The present invention may be embodied in other specific forms without departing from its spirit or essential characteristics. Thus the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for percutaneous infusion of an internal wound site, the system comprising:
   a first reservoir shaped to contain a first fluid;
   a tube having a preferentially distendable portion formed of a single material, wherein at the preferentially distendable portion, distention of a diameter of the tube in response to blockage of the tube is amplified, the preferentially distendable portion having a noncircular cross sectional shape in the absence of blockage of the tube;

a motor operable to urge the first fluid toward the internal wound site via the tube; and a blockage sensor comprising a first conductor in direct contact with the exterior of the tube and a second conductor, wherein at least one of the first and second conductors is configured to be urged into contact with the other to form a switch, the switch configured to be actuated between an open circuit condition and a closed circuit condition in response to direct receipt of mechanical force exerted by distention of the tube;

wherein the switch is operable without the preferentially distendable portion being fully surrounded.

2. The system of claim 1, wherein the blockage sensor and the motor are integrated into a controller configured to automatically control fluid flow from the first reservoir to the internal wound site.

3. The system of claim 2, wherein the distention of the diameter of the preferentially distendable portion is amplified via constraint of the diameter along a direction.

4. The system of claim 3, wherein the controller further comprises a constraining member, wherein the tube is routed about the constraining member to provide the preferentially distendable portion, wherein the direction is generally parallel to a radius about which the tube bends, wherein the blockage sensor measures preferential distention of the preferentially distendable portion along the direction.

5. The system of claim 1, wherein the switch comprises a button displaced from the preferentially distendable portion along the direction such that the preferentially distendable portion presses against the button to move the switch between the open circuit condition and the closed circuit condition in response to distention of the preferentially distendable portion.

6. The system of claim 1, wherein the switch comprises a first conductor attached to the preferentially distendable portion and a second conductor positioned proximate the preferentially distendable portion such that the first conductor is movable into contact with the second conductor to move the switch between the open circuit condition and the closed circuit condition in response to distention of the preferentially distendable portion.

7. The system of claim 1, wherein the switch comprises a conductor and a conductive bridge, wherein the conductive bridge is positioned proximate the preferentially distendable portion such that the conductive bridge is movable between a closed state in which the conductive bridge contacts the conductor to provide the closed circuit condition, and an open state in which the bridge is displaced from the conductor to provide the open circuit condition, in response to distention of the preferentially distendable portion.

8. The system of claim 3, wherein the controller further comprises a peristaltic pump driven by the motor, the peristaltic pump comprising a plurality of rotors that rotate about an axis of rotation of the motor to urge the first fluid to move through the tube.

9. The system of claim 8, wherein the tube is routed tightly about the rotors such that tension in the tube causes opposing sides of the tube to press against each other proximate each of the rotors to impede flow of the first fluid past the rotors.

10. The system of claim 8, wherein the peristaltic pump is configured to deliver a bolus of the first fluid to the internal wound site at a gage pressure of at least ten psi.

11. The system of claim 3, further comprising a second reservoir shaped to contain a second fluid, wherein the controller is further configured to aspirate the internal wound site by urging the second fluid into the second reservoir from the internal wound site.

12. The system of claim 3, wherein the motor has an axis of rotation, and the first reservoir is attachable to the controller along an attachment plane to position the first reservoir alongside the motor, wherein the attachment plane is substantially parallel to at least one of the axis of rotation and an output shaft coupled to the motor to drive a pump.

13. A controller of a system for percutaneous infusion of an internal wound site, the controller comprising:

a motor operable to urge a first fluid from a first reservoir toward the internal wound site via a tube, wherein the motor is further operable to draw a second fluid from the internal wound site; and a blockage sensor that detects blockage of the tube by measuring distention of the tube at a preferentially distendable portion along a direction perpendicular to an axis of the tube, wherein at the preferentially distendable portion the tube is routed such that the tube bends along a substantially arcuate pathway, wherein the blockage sensor comprises a conductor external to the tube, wherein the conductor moves to actuate a switch between an open circuit condition and a closed circuit condition in response to direct receipt of mechanical force exerted by distention of the tube;

wherein the switch is operable without the preferentially distendable portion of the tube being fully surrounded.

14. The controller of claim 13, further comprising a constraining member about which the tube is routed such that the tube bends about a radius to provide the preferentially distendable portion at which the preferential distention is measured, wherein the direction is generally perpendicular to the radius.

15. The controller of claim 13, wherein the blockage sensor comprises a switch positioned to move between an open circuit condition and a closed circuit condition in response to distention of the preferentially distendable portion.

16. The controller of claim 13, wherein the switch comprises a button displaced from the preferentially distendable portion along the direction such that the preferentially distendable portion presses against the button to move the switch between the open circuit condition and the closed circuit condition in response to distention of the preferentially distendable portion.

17. The controller of claim 13, wherein the switch comprises a first conductor attached to the preferentially distendable portion and a second conductor positioned proximate the preferentially distendable portion such that the first conductor is movable into contact with the second conductor to move the switch between the open circuit condition and the closed circuit condition in response to distention of the preferentially distendable portion.

18. The controller of claim 13, wherein the switch comprises a conductor and a conductive bridge, wherein the conductive bridge is positioned proximate the preferentially distendable portion such that the conductive bridge is movable between a closed state in which the conductive bridge contacts the conductor to provide the closed circuit condition, and an open state in which the bridge is displaced from the conductor to provide the open circuit condition, in response to distention of the preferentially distendable portion.

19. The controller of claim 13, wherein the controller further comprises a peristaltic pump driven by the motor, the peristaltic pump comprising a plurality of rotors that rotate about an axis rotation of the motor to urge the first fluid to move through the tube.

20. The controller of claim 19, wherein the tube is routed tightly about the rotors such that tension in the tube causes opposing sides of the tube to press against each other proximate each of the rotors to impede flow of the first fluid past the rotors.

21. The controller of claim 19, wherein the peristaltic pump is configured to deliver a bolus of the first fluid to the internal wound site at a gage pressure of at least ten psi.

22. The controller of claim 13, wherein the motor has an axis of rotation, the controller further comprising a mating surface shaped to receive the first reservoir along an attachment plane to position the first reservoir alongside the motor, wherein the attachment plane is substantially parallel to at least one of the axis of rotation and an output shaft coupled to the motor to drive a pump.

23. A method for detecting blockage of a tube of a system for percutaneous infusion of an internal wound site, the system comprising a controller having a motor operable to urge a first fluid from a first reservoir toward the internal wound site via the tube, the method comprising:
routing a preferentially distendable portion of the tube such that the preferentially distendable portion bends along a substantially arcuate pathway, wherein the preferentially distendable portion is formed of a single material, the preferentially distendable portion having a noncircular cross sectional shape in the absence of blockage of the tube;
distending the preferentially distendable portion to exert mechanical force; and
directly receiving the mechanical force with a switch comprising a first conductor and a second conductor, wherein the mechanical force urges at least one of the conductors into contact with the other to actuate the switch between an open circuit condition and a closed circuit condition to detect blockage of the tube;
wherein the switch is operable without the preferentially distendable portion being fully surrounded.

24. The method of claim 23, wherein the controller further comprises a constraining member, wherein constraining the portion of the tube comprises routing the tube about the constraining member such that the direction is generally parallel to a radius about which the tube bends, wherein detecting blockage of the tube comprises measuring distention of the preferentially distendable portion along the direction.

25. The method of claim 23, wherein the switch comprises a button displaced from the preferentially distendable portion along the direction, wherein moving the switch between the open circuit condition and the closed circuit condition comprises pressing against the button with the preferentially distendable portion in response to distention of the preferentially distendable portion.

26. The method of claim 23, wherein the switch comprises a first conductor attached to the preferentially distendable portion and a second conductor positioned proximate the preferentially distendable portion, wherein moving the switch between the open circuit condition and the closed circuit condition comprises moving the first conductor into contact with the second conductor in response to distention of the preferentially distendable portion.

27. The method of claim 23, wherein the switch comprises a conductor and a conductive bridge, wherein the conductive bridge is positioned proximate the preferentially distendable portion, wherein moving the switch between the open circuit condition and the closed circuit condition comprises moving the conductive bridge between a closed state in which the conductive bridge contacts the conductor and an open state in which the bridge is displaced from the conductor, in response to distention of the preferentially distendable portion.

28. The method of claim 23, wherein the controller further comprises a peristaltic pump driven by the motor, the peristaltic pump comprising a plurality of rotors, the method further comprising rotating the rotors about an axis of rotation of the motor to urge the first fluid to move through the tube.

29. The method of claim 28, further comprising stretching the tube around the rotors such that tension in the tube causes opposing sides of the tube to press against each other proximate each of the rotors to impede flow of the first fluid past the rotors.

30. The method of claim 28, wherein rotating the rotors about the axis of rotation to urge the first fluid to move through the tube comprises delivering a bolus of the first fluid to the internal wound site at a gage pressure of at least ten psi.

31. A system for percutaneous infusion of an internal wound site, the system comprising:
a reservoir module comprising a first reservoir shaped to contain a first fluid; and
a controller designed to receive the reservoir module, the controller comprising a motor and a peristaltic pump driven by the motor to urge the first fluid toward the internal wound site via a tube, the tube having a preferentially distendable portion at which the tube is routed about a fixed constraining member such that a diameter of the tube is constrained along a direction generally parallel to a radius about which the tube bends along a substantially arcuate pathway, the controller further comprising a blockage sensor that detects blockage of the tube by measuring preferential distention of the preferentially distendable portion along the direction.

32. The system of claim 31, wherein the switch comprises a button displaced from the preferentially distendable portion along the direction such that the preferentially distendable portion presses against the button to move the switch between the open circuit condition and the closed circuit condition in response to distention of the preferentially distendable portion.

33. The system of claim 32, wherein the switch is mechanically operated.

34. The system of claim 31, wherein the peristaltic pump comprises a plurality of rotors that rotate about an axis of rotation of the motor to urge the first fluid to move through the tube, wherein the tube is routed tightly about the rotors such that tension in the tube causes opposing sides of the tube to press against each other proximate each of the rotors to impede flow of the first fluid past the rotors.

35. The system of claim 31, wherein the peristaltic pump is configured to deliver a bolus of the first fluid to the internal wound site at a gage pressure of at least ten psi.

36. The system of claim 31, wherein the reservoir module further comprises a second reservoir shaped to contain a second fluid, wherein the controller is further configured to aspirate the internal wound site by urging the second fluid into the second reservoir from the internal wound site.

37. The system of claim 31, wherein the motor has an axis of rotation, and the first reservoir is attachable to the controller along an attachment direction substantially parallel to the axis of rotation to position the first reservoir alongside the motor.

* * * * *

UNITED STATES PATENT AND TRADEMARK OFFICE
CERTIFICATE OF CORRECTION

| | | |
|---|---|---|
| PATENT NO. | : 7,462,163 B2 | Page 1 of 1 |
| APPLICATION NO. | : 10/903951 | |
| DATED | : December 9, 2008 | |
| INVENTOR(S) | : Marc Yap et al. | |

It is certified that error appears in the above-identified patent and that said Letters Patent is hereby corrected as shown below:

Column 9, Lines 46, 48, 50, 53, and 59, DELETE reference numeral "446", ADD "464" for each occurrence of reference numeral 446.

Signed and Sealed this

Twenty-eighth Day of July, 2009

JOHN DOLL
*Acting Director of the United States Patent and Trademark Office*